United States Patent [19]

Kasper et al.

[11] Patent Number: 4,854,995

[45] Date of Patent: Aug. 8, 1989

[54] DELIVERY SYSTEM OF STRIPPABLE EXTRUSION COATED FILMS FOR MEDICAL APPLICATIONS

[75] Inventors: Klaus B. Kasper, Pulaski; Tom Yip, Central Square, both of N.Y.

[73] Assignee: Bertek, Inc., Swanton, Vt.

[21] Appl. No.: 96,274

[22] Filed: Sep. 9, 1987

Related U.S. Application Data

[63] Continuation of Ser. No. 813,791, Dec. 27, 1985, abandoned.

[51] Int. Cl.$^4$ .............................................. B29C 47/06
[52] U.S. Cl. ................................... 156/243; 128/156; 156/244.11; 264/171; 264/216; 264/233; 264/331.18; 264/344
[58] Field of Search ................ 264/171, 231.18, 233, 264/344, 49, 216; 128/156; 425/131.1; 156/182, 241, 243, 244.11

[56] References Cited

U.S. PATENT DOCUMENTS

| | | | |
|---|---|---|---|
| 3,426,754 | 2/1969 | Bierenbaum et al. | 128/156 |
| 3,645,835 | 5/1985 | Hodgson | 428/40 |
| 3,775,239 | 11/1973 | Snow | 264/171 |
| 3,844,865 | 10/1974 | Elton et al. | 264/210.6 |
| 4,018,951 | 4/1977 | Gross | 264/331.18 |
| 4,034,751 | 7/1977 | Hung | 264/344 |
| 4,076,673 | 2/1978 | Burkholder, Jr. | 264/344 |
| 4,265,234 | 5/1981 | Schaar | 128/156 |
| 4,310,593 | 1/1982 | Gross | 264/331.18 |
| 4,367,732 | 1/1983 | Poulsen et al. | 128/156 |
| 4,370,981 | 2/1983 | Sanderson | 128/334 |
| 4,379,806 | 4/1983 | Korpman | 264/171 |
| 4,413,621 | 11/1983 | McCracken et al. | 128/156 |
| 4,516,571 | 5/1985 | Buchan | 128/132 R |

FOREIGN PATENT DOCUMENTS

| | | | |
|---|---|---|---|
| 58-05226 | 1/1983 | Japan | 264/171 |
| 58-20421 | 2/1983 | Japan | 264/171 |
| 58-38778 | 3/1983 | Japan | 264/171 |

*Primary Examiner*—Jeffery Thurlow
*Attorney, Agent, or Firm*—Smith & Schnacke

[57] ABSTRACT

The present invention provides a process for producing a wound dressing delivery system. The wound dressing delivery system is formed by extruding first and second thermoplastic resins onto the surface of a carrier sheet to form first and second thermoplastic films; the first thermoplastic film functions as a temporary support for the second thermoplastic film and the second thermoplastic film functions as a wound dressing and has a moisture vapor transmission rate of greater than 300 grams/square meter/24 hours (ASTM E-96:37.8° C./90% R.H.). The first thermoplastic resin is extruded onto the surface of the carrier sheet and the second thermoplastic resin is extruded onto the surface of the first thermoplastic film such that the first thermoplastic film is interposed between the carrier sheet and the second thermoplastic film.

11 Claims, 2 Drawing Sheets

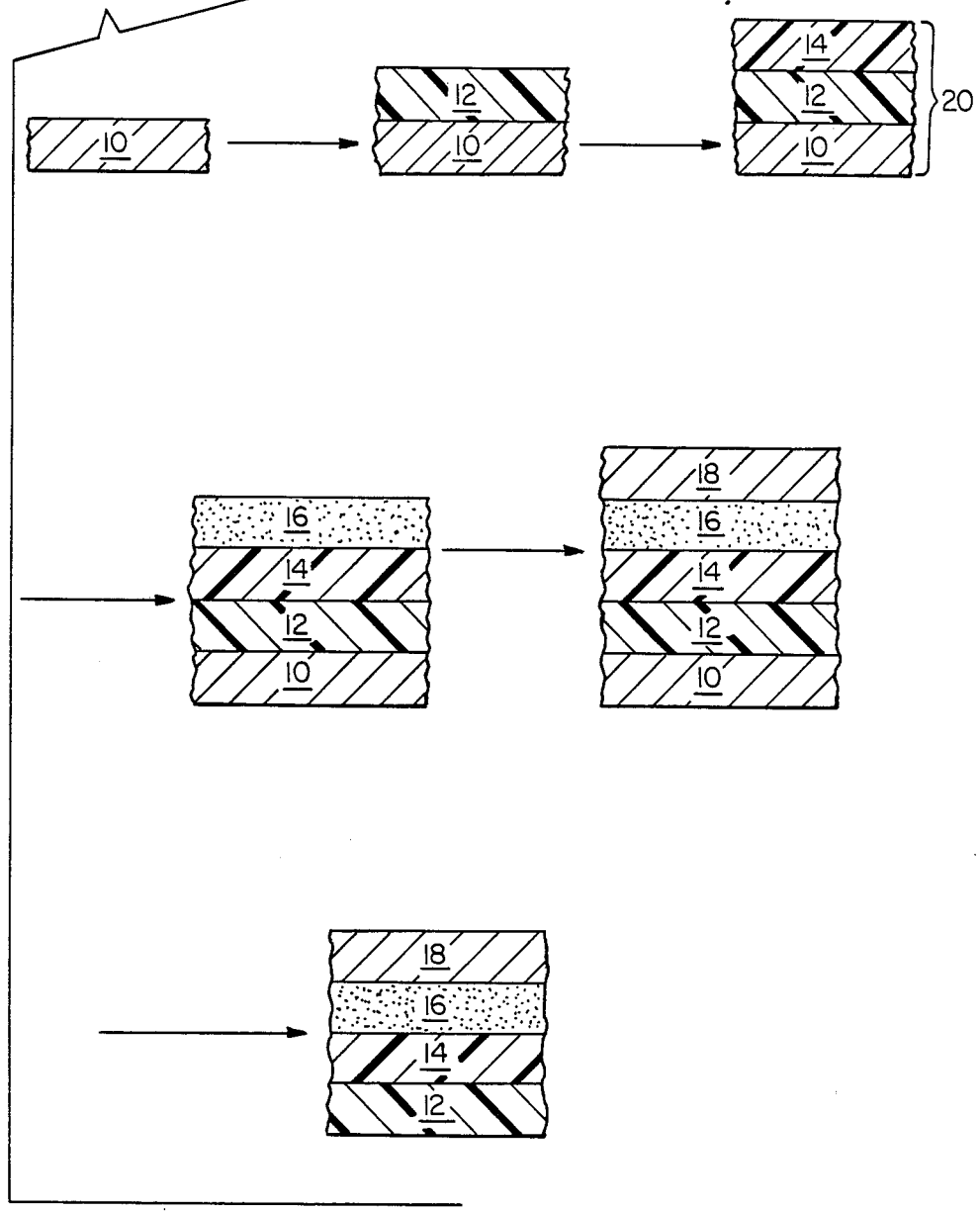

DELIVERY SYSTEM OF STRIPPABLE EXTRUSION COATED FILMS FOR MEDICAL APPLICATIONS

This is a continuation, of co-pending application Ser. No. 813,791, filed Dec. 27, 1985, now abandoned.

BACKGROUND OF THE INVENTION

The present invention relates to a process for producing a wound dressing delivery system.

Recent approaches to the production of wound dressings focus on the concept of moist wound healing. Experimental work indicates that the regrowth of epithelial tissue on a wound occurs more rapidly under moist conditions. The environment which promotes such tissue regrowth depends on the adherence, the bacterial barrier, the oxygen transportation, and the water vapor transportation of the wound dressing.

Adherent wound dressings which, in their simplest form, consist of an oxygen and moisture vapor permeable film which is adhered to the wound site by an adhesive of similar permeability, have been designed. These dressings are both occlusive and permit the free flow of oxygen and other gases through the wound dressing. An important consideration in designing the films used in these dressings is the level of oxygen and moisture transmission through the layers of an adherent wound dressing. The advantages of a high percentage of oxygen transmission through the wound dressing are that the oxygen is made available to both the white blood cells in the wound and also to the newly-grown tissue on the wound surface for the purpose of maintaining functional viability through aerobic metabolism. Moisture permeability permits the wound to breathe and sweat normally.

An example of an adhesive backed polyurethane occlusive dressing is disclosed in U.S. Pat. No. 3,645,835 to Hodgson. The dressing comprises a backing material which is an unreinforced thermoplastic polyurethane film, having a pressure-sensitive adhesive on one face for binding the film to the wound site. Suitable thermoplastic polyurethane film is made by extrusion or by solvent casting. The adhesive may be applied to the polyurethane film in solution, as an aqueous dispersion, as a hot melt, or by a transfer process. Under the convenient transfer process, the adhesive solution is spread on release-coated paper, and almost dried before contacting the polyurethane film under sufficient pressure to ensure good contact. The release paper is then removed. The dressing is water vapor permeable but not liquid water permeable. The dressing has a moisture vapor transmission rate of at least 300 grams/square meter/24 hours/40° C./80% R.H.

Other medical dressings include that disclosed in U.S. Pat. No. 3,426,754 to Bierenbaum et al. The dressing comprises a backing and a pressure-sensitive adhesive coating. The preferred backing is an olefin polymer. To prepare a suitable backing, the backing is extruded and then drawn to impart an open-celled structure and to reduce the apparent density. The open-celled structure permits maximum gas permeability. The adhesive may then be applied to the backing in any way which prevents adhesive penetration through the backing after the adhesive is dried.

U.S. Pat. No. 4,367,732 to Poulsen et al. discloses a skin barrier wherein a silicone release paper is overcoated with polyethylene, an elastic film, and an elastic adhesive. A silicone release paper may be optionally secured to the elastic adhesive. The elastic film and the elastic adhesive in combination function as the claimed skin barrier. The preferred elastic film is a polyurethane film. The elastic adhesive is a mixture of a crosslinked elastomer, a hydrocarbon tackifier resin, a polar plasticizer, an antioxidant, an oily extender, and a hydrocolloid. The support material and the optional silicone release paper are removed prior to use.

U.S. Pat. No. 4,516,571 to Buchan discloses a medical dressing which is filled with polyurethane gel and has walls formed from polyetherpolyamide block copolymer film. An adhesive may be coated on the body contacting surface of the film. The dressing has a water vapor transmission rate of greater than 300 grams/square meter/24 hours at 37° C. at 100% to 10% relative humidity. The film may be formed into strips of the appropriate size, folded, and heat sealed along the sides to provide an envelope with an opening; the envelope may also be blow molded or vacuum formed. The polyurethane gel is then transferred to the polyetherpolyamide block copolymer envelope and the envelope is closed by heat sealing.

Understandably, the products, which result when the aforementioned properties are taken into consideration, are skin-like in appearance and in their physical characteristics. These properties make the products difficult to handle, particularly in large formats, during manufacturing. The present invention is directed to a process for manufacturing films useful as a wound dressing on a carrier sheet. In accordance with the present invention, the films are extrusion coated onto a carrier sheet. This intermediate product may then be shipped to a manufacturer for application of an adhesive coating, which may be medicated, and an adhesive liner. The carrier sheet is then readily removed for packaging.

SUMMARY OF THE INVENTION

An object of the present invention is to provide a process for producing a wound dressing delivery system in which the wound dressing is readily handled during manufacturing.

In accordance with the present invention, the wound dressing delivery system is formed by extruding first and second thermoplastic resins onto the surface of a carrier sheet to form first and second thermoplastic films; the first thermoplastic film functions as a temporary support for the second thermoplastic film and the second thermoplastic film functions as a wound dressing having a moisture vapor transmission rate of greater than 300 grams/square meter/24 hours (ASTM E-96:37.8° C./90% R.H.). The first thermoplastic resin is extruded onto the surface of the carrier sheet and the second thermoplastic film is extruded onto the surface of the first thermoplastic film such that the first thermoplastic film is interposed between the carrier sheet and the second thermoplastic film.

BRIEF DESCRIPTION OF THE DRAWINGS

FIG. 1 is a schematic illustration of three stages in the preparation of a wound dressing delivery system in accordance with the present invention.

FIG. 2 is a schematic illustration of the preparation of a wound dressing delivery system in accordance with the present invention.

DETAILED DESCRIPTION OF THE INVENTION

Figure 1A:
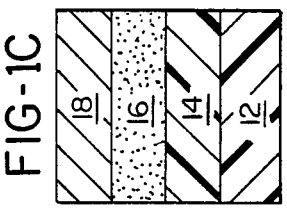
FIG. 1A is a schematic illustration of a wound dressing delivery system in accordance with the present invention.

FIG. 1A illustrates a wound dressing delivery system in accordance with the present invention in its simplest form. The delivery system 20 includes a carrier sheet 10, a first thermoplastic film 14, and a second thermoplastic film 14. The second thermoplastic film is moisture vapor permeable and functions as the ultimate wound dressing. The first film functions as a support for the second and provides strength and body which make the second film easier to handle and apply to the wound.

Figure 1B:
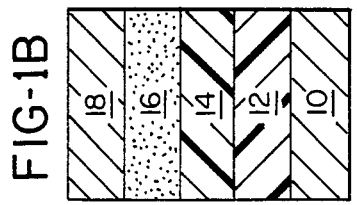
FIG. 1B is a schematic illustration of the wound dressing delivery system after application of an adhesive and a release sheet.
Figure 1C:
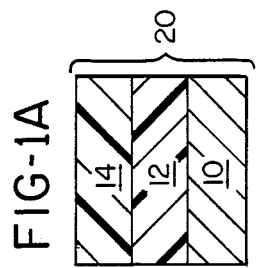
FIG. 1C is a schematic illustration of the wound dressing delivery system after removal of the carrier sheet.

The delivery system 20 will be further processed by applying a layer of adhesive 16 and a release sheet 18 thereto as shown in FIG. 1B. Prior to packaging, the carrier sheet 10 is removed to yield the structure shown in FIG. 1C. To use the wound dressing, the release sheet 18 is removed from the adhesive 16 and the dressing with the adhesive side down is placed over the wound. The film 12 is then stripped from the dressing.

The requirements of the carrier sheet include strength and a fairly uniform surface because the thermoplastic films are extruded directly onto the surface of the carrier sheet. A variety of materials can be used for this purpose, but a carrier sheet particularly useful in the present invention is paper. The nature of the paper web is not critical and bleached and unbleached Kraft sheets are suitable. The paper has to be strong enough to go through the extrusion coating process and the subsequent processing operations. Papers in the basis weight range from 70–110 gr/m$^2$ have been used, but papers from 50–250 gr/m$^2$ should also be suitable.

Various thermoplastic resins are useful in forming the first thermoplastic film. Representative examples include polyolefins and, in a more preferred embodiment, polypropylene.

Useful thermoplastic resins which may be used to form the second thermoplastic film 14 include polyetherpolyamide block copolymers, polyurethanes, and copolyesters. Thermoplastic resins useful in the second thermoplastic film are commercially available. An example of a polyetherpolyamide block copolymer useful in the second thermoplastic film of the present invention is available from Ato Chimie, under the designation Pebax. Examples of polyurethanes useful in the second thermoplastic film of the present invention are available from Upjohn, under the designation Pellathane, and available from K. J. Quinn, under the designation Q-Thane. Examples of copolyesters useful in the second thermoplastic film of the present invention are available from Eastman Chemicals, under the designation PCCE, and available from DuPont, under the designation Hytrel.

A specific example of a polyetherpolyamide block copolymer useful in forming a wound dressing delivery system in accordance with the present invention is Pebax 3533 SN00. Specific examples of polyurethanes useful in forming a wound dressing delivery system in accordance with the present invention include Pellathane 2363-80AE and Q-Thane PS-38. Specific examples of copolyesters useful in forming a wound dressing system in accordance with the present invention include PCCE 9966 and Hytrel 4056.

A critical characteristic of the second thermoplastic film is the water vapor transmission rate. The thickness and nature of the second thermoplastic film employed in the present wound dressing delivery system are selected to provide the desired water vapor transmission rate. The film is chosen so that its water vapor transmission rate is greater than 300 grams/square meter/24 hours (ASTM E-96:37.8° C./90% R.H.) and preferably will be greater than 500 grams/square meter/24 hours (ASTM E-96:37.8° C./90% R.H.). Typically, the film 14 is about 0.2 to 7 mils thick.

The thickness of film 12 is less critical. The thickness is selected such that the wound dressing is easily handled and readily conforms to the wound. Typically, film 12 will range from about 0.5 to 10 mils in thickness.

Figure 3:
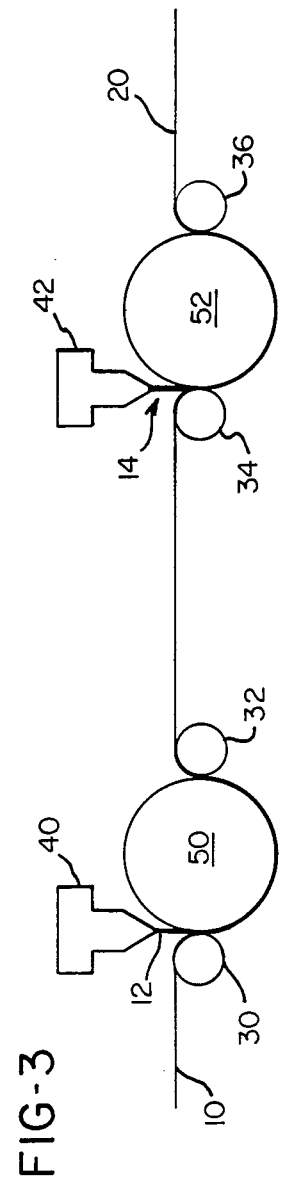
FIG. 3 is a schematic illustration of one process for producing a wound dressing delivery system in accordance with the present invention.

To manufacture the delivery system, thermoplastic film 12 is extruded onto the surface of the carrier sheet 10. As shown in FIG. 3, a web of carrier sheet 10 is fed from a roll (not shown) into a nip formed between the chill roll 50 and rubber roll 30. Carrier sheet 10 travels at a velocity of about 50' to 1000' feet/minute under the extruder 40. The pressure in the nip of chill roll 50 and rubber roll 30 is preferably in the operating range of about 50 to 75 psi for web width of 45–60".

The thermoplastic resin is maintained at an extrusion melt temperature and is extruded from extruder 40 as a film 12 into the nip formed by chill roll 50 and rubber roll 30 to form the laminate shown in FIG. 2. The design of the extruder is not critical in general. More important is the screw design which must be suitable for the particular resin. Power requirements and gear ratios are also determined by the viscosity of the resin and have to be adjusted accordingly. Most extruders suitable for polyolefins can be adapted to also extrude the elastomeric medical resins. A specialty extruder is generally not required. The extruder size is determined by output requirements more than anything else. Extruder diameters from 2½ to 6 inches are usually adequate. The length over diameter or L/D ratio which is an important factor in extruder design should be no less than 24/1 and is optimally 30/1 or 32/1.

The extrusion temperatures can be varied widely and is actually one of the parameters that is used in achieving controlled release forces. The higher the extrusion coating temperature, the more oxidation of the film takes place when it leaves the extruder and before it is laminated to the paper or the film. Oxidation of the film surface is the major factor which determines the surface energy which in turn determines the release force between film and paper or film and film. Corona treatment of the paper and/or the first film surface (after it has been extruded and laminated to the paper) can be used to adjust oxidation, surface energy, and release force.

Normally, the temperature of thermoplastic film 12 as it enters the nip is above its melting point of 400° to 625° F. As shown in FIG. 3, thermoplastic film 12 adhered to carrier sheet 10 is wrapped around chill roll 50 by rubber roll 30 and take off roll 32. The chill roll 50 operates at a temperature of about 40° to 120° F. Contact with chill roll 50 cools and sets thermoplastic film 12.

Thermoplastic film 14 is extruded onto the surface of thermoplastic film 12 at extruder 42. Carrier sheet 10 functions to support thermoplastic film 12 and thermoplastic film 14 during the manufacturing process. As shown in FIG. 3, carrier sheet 10 and adhered thermoplastic film 12 feed into a nip formed by chill roll 52 and rubber roll 34. The pressure in the nip of chill roll 52 and rubber roll 34 is in the preferred operating range of about 50 to 75 psi for 45-60" web width.

Thermoplastic resin which is maintained above the extrusion melt temperature, is extruded from extruder 42 in a thermoplastic film 14 into the nip formed by chill roll 52 and rubber roll 34. The resulting thermoplastic film is applied at a rate of about 10 to 150 grams/square meter. Chill roll 52 operates at a temperature of about 75° to 90° F. Contact with chill roll 52 cools and sets thermoplastic film 14. Intermediate 2 is stripped from chill roll 52 by roll 36, and proceeds to a winder (not shown).

As shown in FIG. 2, intermediate 20 may be further processed by the application of adhesive coating 16 over thermoplastic film 14, and lamination of adhesive release liner 18 over adhesive coating 16 in an otherwise conventional manner.

Suitable adhesives useful in the present invention must be compatible with the skin and thus will normally be hypo-allergenic. Preferably, the adhesives will be synthetic polymers or mixtures thereof. Such adhesives may be selected from those described in British Patent Specification No. 1280631 and European patent application No. 35399, both of which are incorporated herein by reference. Preferred adhesives are those which have a moisture vapor transmission rate such that the adhesive, together with the second thermoplastic film, has a moisture vapor transmission rate of greater than 300 grams/square meter/24 hours and, more preferably, greater than 500 grams/square meter/24 hours when measured at 37° C. and 100% to 10% relative humidity. Suitable adhesives include those formed from polyacrylates or polyvinyl ethers. Commercially available adhesives that may be used include Avery's 351, Monsanto's 2333 and RA-737.

The release liner 18 may be formed from conventional materials such as silicone release paper, silicone coated films, or Quilon coated release papers or films, depending upon the aggressiveness of the adhesive.

EXAMPLE

An intermediate useful in a wound dressing system was prepared using the process described with respect to FIG. 2 and 3. A 110 gr/m² weight paper was fed into a nip at a velocity of 300' feet/minute. The nip pressure was 60 psi.

Polypropylene resin, which was maintained at a melt temperature of 550° F., was extruded in a polypropylene film onto the paper. The coating speed was 300' feet/minute and the resulting polypropylene coating was 17 grams/square meter or 0.7 mils thick. The chill roll temperature was 60° F.

The paper and adhered polypropylene film were conveyed into the second nip between roll 34 and chill roll 52 with a pressure of 60 psi. Polyetherpolyamide block copolymer, Pebax 3533 SN00, available from Ato Chimie, was extruded from extruder 42 to form the second thermoplastic film. The copolymer was maintained at a melt temperature of 350° F. and extruded onto the polypropylene film. The coating speed was 300' feet/minute and the resulting film coat weight was 30 grams/square meter or 1 mil in thickness. The temperature of chill roll 52 was 45° F.

A polyacrylate adhesive coating was applied over film 14 and a silicone release liner 18 was laminated over adhesive 16. The paper support 10 was then stripped off and the remaining laminate is ready for packaging.

Having described the invention in detail and by reference to preferred embodiments thereof, it will be apparent that numerous modifications and variations are possible without departing from the spirit and scope of the following claims.

What is claimed is:

1. A process for producing a wound pressing delivery system comprising the steps of:

extruding first and second thermoplastic resins onto the surface of the carrier sheet to form first and second thermoplastic films, said first thermoplastic film functioning as a temporary support for said second thermoplastic film and being capable of releasing from said second thermoplastic film and said second thermoplastic film being useful as a wound dressing and having a moisture vapor transmission rate of greater than 300 grams/square meter/24 hours (ASTM E-96:37.8° C./90% R.H.); said first thermoplastic resin being extruded onto the surface of said carrier sheet and said second thermoplastic film being extruded directly onto the surface of said first thermoplastic film without the aid of an adhesive such that said first thermoplastic film is interposed between said carrier sheet and said second thermoplastic film.

2. The process of claim 1 wherein said first thermoplastic film is a polyolefin.

3. The process of claim 2 wherein said first thermoplastic film is polypropylene.

4. The process of claim 2 wherein said second thermoplastic film is a polyetherpolyamide block copolymer.

5. The process of claim 2 wherein said second thermoplastic film is a polyurethane.

6. The process of claim 2 wherein said second thermoplastic film is a copolyester.

7. The process of claim 2 wherein sad second thermoplastic film has a water vapor transmission rate of at least 500 grams/square meter/24 hours (ASTM E-96:37.8° C./90% R.H.).

8. The process of claim 7 additionally comprising the steps of:

applying an adhesive coating and an adhesive release liner onto the surface of said second thermoplastic film wherein said adhesive coating functions to adhere said wound dressing delivery system to a wound area and said adhesive release liner functions to protect said adhesive coating; said adhesive coating being applied to the surface of said second thermoplastic film and said adhesive release liner being laminated over the surface of said adhesive coating such that said adhesive coating is interposed between said second thermoplastic film and said adhesive release liner.

9. The process of claim 8 wherein the release force between said first thermoplastic film and said carrier sheet is greater than the release force between said first thermoplastic film and a chill roll.

10. The process of claim 9 wherein the release forces between said first and second thermoplastic films is greater than the release force between said second thermoplastic film and a chill roll.

11. A process for producing a wound dressing delivery system comprising the steps of extruding polypropylene and polyetherpolyamide block copolymer onto the surface of a paper sheet to form a film of said polypropylene and said polyetherpolyamide block copolymer, said polypropylene functioning as a temporary support for said polyetherpolyamide block copolymer and said polyetherpolyamide block copolymer being useful as a wound dressing and having a moisture vapor transmission rate greater than 300 grams/square meter/24 hours; said polypropylene being extruded onto the surface of said paper sheet and polyetherpolyamide block copolymer being extruded onto the surface of said polypropylene such that said polypropylene is interposed between said paper sheet and said polyetherpolyamide block copolymer.

* * * * *